(12) United States Patent
Woodward

(10) Patent No.: US 6,579,497 B2
(45) Date of Patent: Jun. 17, 2003

(54) DISPENSING METHOD AND APPARATUS FOR DISPENSING VERY SMALL QUANTITIES OF FLUID

(75) Inventor: Roger P. Woodward, Portsmouth, VA (US)

(73) Assignee: First Ten Angstroms, Portsmouth, VA (US)

( * ) Notice: Subject to any disclaimer, the term of this patent is extended or adjusted under 35 U.S.C. 154(b) by 0 days.

(21) Appl. No.: 10/238,592

(22) Filed: Sep. 11, 2002

(65) Prior Publication Data
US 2003/0049863 A1 Mar. 13, 2003

Related U.S. Application Data

(63) Continuation-in-part of application No. 09/950,700, filed on Sep. 13, 2001.

(51) Int. Cl.[7] .................................................. B01L 3/02
(52) U.S. Cl. ...................... 422/66; 73/864.11; 422/100; 436/44; 436/54; 436/180
(58) Field of Search ...................... 422/66, 100; 436/44, 436/54, 180; 73/864.11

(56) References Cited

U.S. PATENT DOCUMENTS

| | | | | |
|---|---|---|---|---|
| 5,312,757 A | * | 5/1994 | Matsuyama et al. | 436/54 |
| 5,555,767 A | * | 9/1996 | Makino et al. | 73/863 |
| 5,811,306 A | * | 9/1998 | Komatsu | 436/54 |
| 5,856,200 A | * | 1/1999 | Krause et al. | 436/180 |
| 6,083,762 A | * | 7/2000 | Papen et al. | 436/180 |
| 6,405,609 B1 | * | 6/2002 | Richards et al. | 73/864.14 |
| 6,484,556 B1 | * | 11/2002 | Jabobs et al. | 73/1.74 |

* cited by examiner

Primary Examiner—Jan Ludlow
(74) Attorney, Agent, or Firm—Whitham, Curtis & Christofferson, PC

(57) ABSTRACT

A fluid dispensing system and method includes a pump to aspirate and expel sample fluid, a fluid dispensing tip, and a metering station. The fluid dispensing tip includes a working fluid and an air gap where the air gap separates the working fluid from the sample fluid. The metering station receives a drop of sample fluid that is at least twice as large as the predetermined volume to ultimately be dispensed. The fluid dispensing tip then withdraws the predetermined volume of fluid from the sample fluid. Precise volumes are ascertained by prior knowledge of the geometry of the fluid dispensing tip and by using an imaging device to monitor an interface of either the sample fluid or working fluid with the air gap within the fluid dispensing tip. The system and method are capable of accurately dispensing very small volumes of sample fluid on the order of 10 picoliters. In addition, the system and method do not require large volumes of sample fluid to prime a pump mechanism.

11 Claims, 7 Drawing Sheets

US 6,579,497 B2

DISPENSING METHOD AND APPARATUS FOR DISPENSING VERY SMALL QUANTITIES OF FLUID

CROSS-REFERENCE TO RELATED APPLICATIONS

This application is a continuation-in-part (CIP) application of U.S. Ser. No. 09/950,700 filed Sep. 13, 2001. The complete contents of the parent application is incorporated herein by reference.

DESCRIPTION

Background of the Invention

1. Field of the Invention

The invention pertains to methods and dispensing apparatuses providing precise, very small quantities of fluids.

2. Description of the Prior Art

It is important in a variety of industries, such as medical diagnostics, biotechnology, and scientific instrumentation, to accurately dispense very small drops of fluids. Furthermore, it is desirable to be able to program the volume of the drops so that the amount delivered will be precise and accurate while at the same time minimizing the amount of a sample required for the dispenser. Some examples of small volume dispensing devices are described in U.S. Pat. Nos. 5,366,896; 5,919,706; 5,927,547; 5,958,342; 5,998,218; 6,083,762; 6,090,348; and 6,100,094. Ink jet printer devices represent an example of a technology area where systems and methods for dispensing small volumes of fluid have been developed. However, the ink jet printer devices suffer from the drawback that they often require several microliters of fluid to prime the dispenser passage; even if only sub-nanoliter sized droplets are dispensed. In many technologies, it would be advantageous to be able to aspirate a volume of about a nanoliter or less without needing to pick up larger amounts. This problem is especially acute in forensic sciences and in biotechnology where only limited quantities of sample are available.

One difficulty with dispensing small volumes of fluid is the necessity of a tip with a small radius. The small radius results in large internal pressures that prevent the fluid from flowing easily from the tip. To overcome this limitation, other systems expel fluids by forcibly ejecting the droplets at a high velocity. However, these systems suffer from accuracy problems. It would be desirable for a system to be able to aspirate and deliver small volumes without being susceptible to clogging, while still maintaining a high level of accuracy.

SUMMARY OF THE INVENTION

It is an object of this invention to overcome the limitations of the prior art, and to provide a highly accurate dispensing device and method which allows dispensing controllable droplets of sub nanoliter size without requiring relatively large priming volumes.

This invention contemplates the use of a pipette or probe that includes a working fluid, an air gap, and a sample fluid in the dispensing tip. The pipette or probe is used to first retrieve a quantity of the sample fluid at the tip. In the retrieval, the working fluid and air gap rise within the pipette or probe, and the sample fluid fills the end of the tip. Then, the invention contemplates dispensing a sessile drop onto a substrate. Preferably, a small portion of the sample remains in the end of the tip, and the tip contacts the outer periphery of the sessile drop. A camera or other imaging device is used to measure the diameter and height of the fluid. This information is then used to calculate the volume inside the tip while it is still in contact with the sessile drop. Then, precise amounts of fluid in selectively variable quantities are drawn back up into the pipette tip from the sessile drop. The tip is then moved to a desired dispensing location, and the desired sample fluid is expelled from that remaining in the tip.

Physically, movement of fluid into a very narrow channel pipette or probe tip is difficult to achieve. The technique utilized in this invention promotes the ability to siphon up sample fluid by different mechanisms. First, creating a sessile drop physically provides a fluid with a surface of curvature that will promote siphoning. Laplace's rule states that the pressure across an interface is proportional to interfacial (surface) tension and inversely proportional to radius of curvature. The small radii inside pipette tips, therefore, leads to large pressures. Second, the liquid surface does not move smoothly over the pipette inside surface because the surface is not energetically constant (i.e., even) and because of what is known as contact angle hysteresis (advancing angles are not equivalent to receding angles). For these reasons, fluid motion is not steady; rather it is stop and start, and may often be referred to as stick/slip. Combined with the high and variable pressures from LaPlace's rule, it is extremely difficult to directly draw or dispense a specific amount from a continuum of liquid.

The genesis of the invention is that the dispense volume is separated from the larger supply volume in a preparatory step before the actual dispense phase. The dispense volume is contained in the end of a capillary tube, separated by an airgap from any system liquid in the pumping system. The exact volume of dispense liquid is set by adjusting the dispense volume while the tip is immersed in a sessile drop of the same liquid. The sessile drop has much larger radii of curvature than the liquid in the tip, and these larger radii lower the interfacial pressure following Laplace's rule.

When one ponders any dispense operation, there are the following two phases: setting the volume to dispense, and detaching the dispensed volume from the remainder of the liquid. This is so basic that it is ordinarily not enunciated. Ordinarily both functions are performed by the same means, and often at the same or very similar times. This is true whether one considers classical syringe pumps or modern ink-jet printer mechanisms. The current invention takes a different and unique approach in that it separates the two phases. As a simplistic analogy, the first phase can be thought of as a "ruler" to set or measure the volume and the second phase can be thought of as "scissors" to separate the volume from its parent or source. This invention separates the ruler from the scissors. Furthermore, there are two kinds of scissors used.

First Phase: The ruler function is performed by video image analysis while the tip is immersed in the sessile drop. The airgap that is set above the liquid in the tip both permits the accurate volume determination through the transparent capillary and is preparatory to the detachment phase. The detachment phase is now subdivided into two portions. This is important. The first occurs when the tip is pulled up from the sessile drop. The tip breaks clean of the sessile drop because the tip is very small. The same Laplace pressures that bedevil us elsewhere ensure that the tip comes out clean, without a hanging pendant drop. The dispense volume is exactly what is inside the tip and what was measured by video analysis. The impetus for the first portion of the detachment is the motor driving the tip up and down. Most importantly, it is not the pump proper. The pump is not able to perform this detachment. So instead, the motorized Z stage separates the "child" volume (the small volume of sample to be dispensed) from the "parent" volume (the volume of the sessile drop).

Second Phase: The pump plays a role in the second portion, which occurs later when the tip is disposed over the target. The pump pushes the dispense liquid out of the tip, either rapidly or slowly, as the user desires. There are applications for all kinds of dispense momentums, or momenta.

In summary, the Z motor provides the scissors between the liquid in the tip and the liquid in the sessile drop. The pump provides the scissors between the airgap and the dispensed volume over the target. The larger radius of the sessile drop used in this invention lowers the pressures, and the high frequency vibrations contemplated by this invention breaks loose the stick/slip motion. In addition, this invention contemplates providing vibrations to the pipette or probe tip. This can be achieved by acoustic or mechanical means (e.g., a piezo ceramic element may be driven to sequentially compress and de-compress the working fluid).

The method and apparatus of this invention are adaptable to robotic placement of very small fluid samples at precise locations. This may have application in certain antibody and DNA detection chips, as well as in a variety of other applications. For example, by having precise quantities of fluid containing an antigen or antibody or single stranded DNA or any other molecular entity placed on a chip or other substrate, it would be possible to optically assess weight differentials which are the result of selective bonding or hybridizing reactions.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
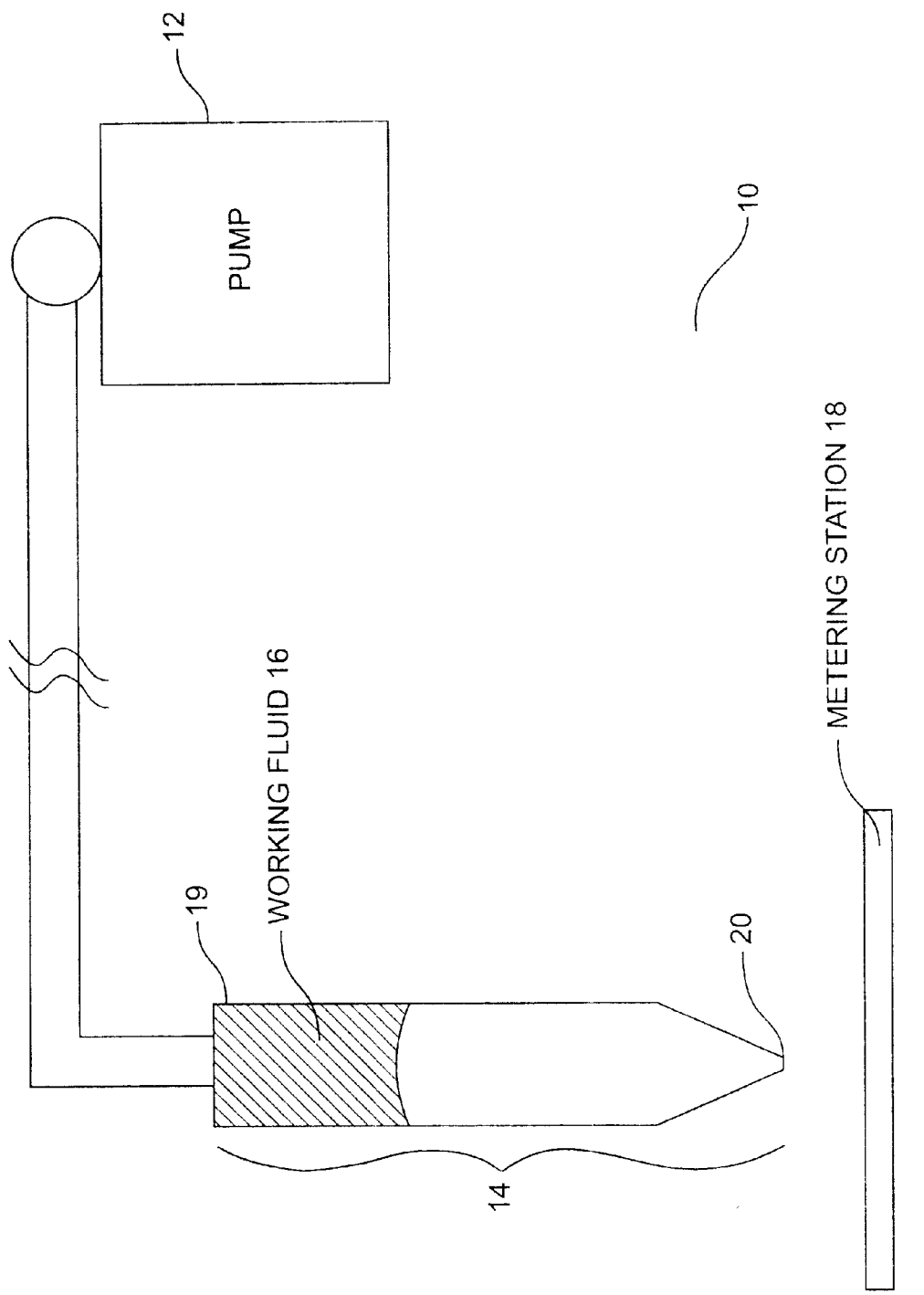
FIG. 1 is a schematic view of a fluid dispensing system embodying the invention.

As illustrated in FIG. 1, the main components of the system 10 include a pump 12, a fluid dispensing tip 14, a working fluid 16, and a metering station 18. The pump 12 functions as a mechanical displacement pump for the purpose of aspirating and dispensing fluid through fluid dispensing tip 14. The resolution of the pump 12 can vary according to the desired size of dispensed droplets. Preferably, the pump 12 is adapted to aspirate volumes on the order of 100 nanoliters or one microliter, but can also aspirate volumes as small as on the order of 10 picoliters. Suitable pumps may include piezo-electric driven diaphragm pumps, such as the FTA 4000 available from First Ten Angstroms of Portsmouth, Va. A preferred embodiment of the pump 18 will be discussed in detail below.

The fluid dispensing tip 14 is used to dispense specified volumes of fluid. Preferably, the tip 14 is adapted to dispense droplets on the order of 10 picoliters. The inner diameter of the base 19 of the tip 14 can range from about 100 $\mu$m to 1000 $\mu$m, but it is preferably 400 $\mu$m. Preferably the tip 14 is conical in shape and is narrower at the end 20 with an inner diameter ranging from about 2 $\mu$m to 20 $\mu$m. One advantage of having a tip 14 with a wider base 19 is the improved ability of the pump 12 to adjust the level of the fluids within the tip 14. The conical shape minimizes viscosity induced pressures because most of the tube is relatively large, it also accommodates a large range of volumes within the field of view of the camera (imaging device 40) used in the practice of this invention. The tip 14 is preferably transparent for inspection purposes. Inspection may be performed by an imaging device 40 such as a video recorder or visually by an operator or by automatic computer analysis. The tip 14 may be made of any material that is not adversely affected by the fluid to be dispensed. Preferred materials include plastic and glass. Some examples of preferred embodiments include a drawn glass capillary or a fused silica fine bore tube, as discussed in more detail below.

A working fluid 16 is contained in the base 19 of the fluid dispensing tip 14. The working fluid 16 may be any fluid that will neither damage the pump 12 nor affect the measurement of the fluid to be dispensed. The working fluid 16 may be the same as the fluid that is to be dispensed. Preferably the working fluid is water. An air gap will always separate the working fluid from the sample.

The metering station 18 is an inert surface that is adapted to receive a drop of the dispensed fluid. The inert surface is defined to be a material that will neither absorb nor significantly react physically or chemically with the fluid to be dispensed. Preferably, the metering station 18 is made of a material that will cause the dispensed fluid to bead on the surface of the metering station 18 (e.g., the metering station 18 may be hydrophobic if the fluid to be dispensed is water-based). The preferred example of a metering station 18 is a polytetrafluoroethylene surface (PTFE commonly referred to as Teflon®). The size of the metering station 18 may vary as long as the metering station 18 is large enough to receive a drop of the fluid to be dispensed. In a preferred embodiment discussed in detail below, the metering station can be positioned below the dispensing tip 14 on an automated basis.

Figure 2:
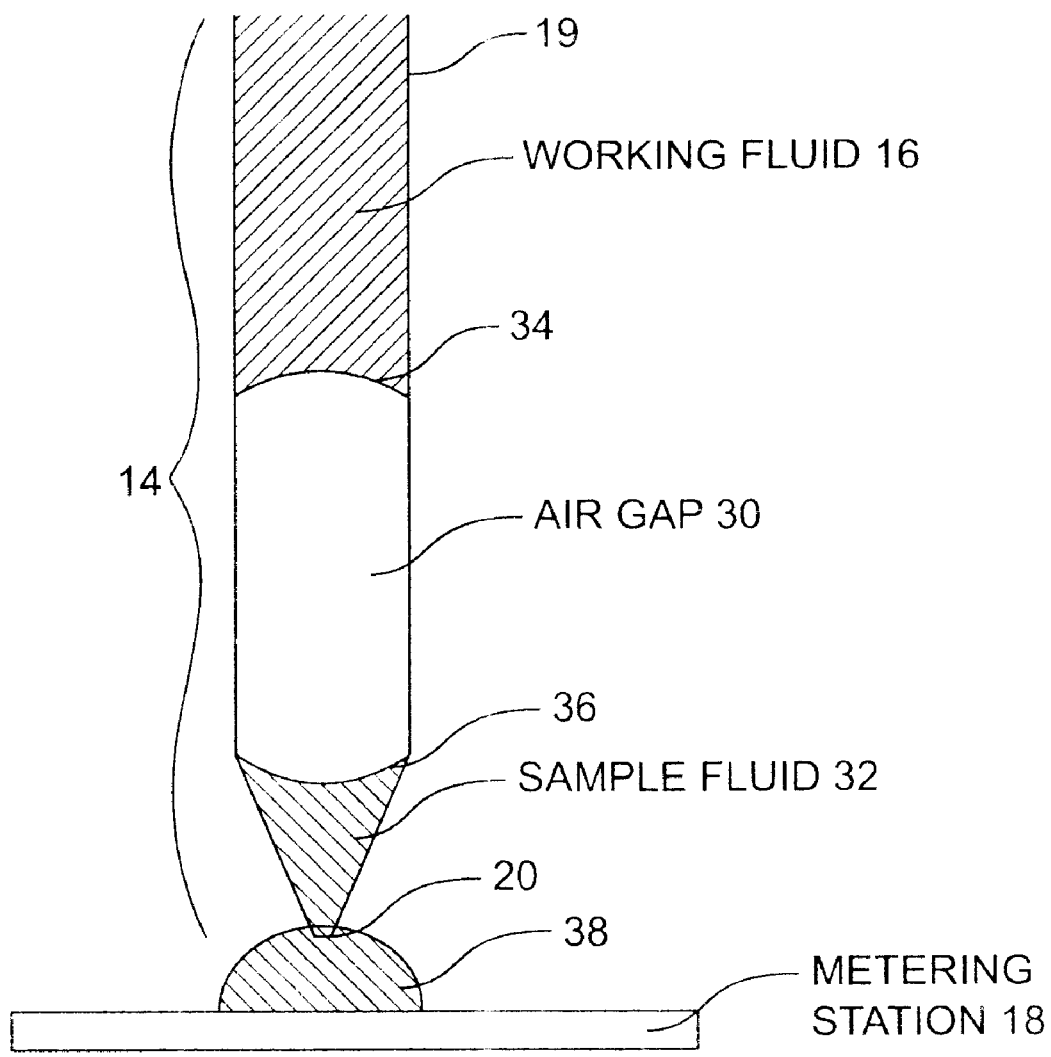
FIG. 2 is a schematic view of the tip depositing a drop of sample fluid onto the metering station.

The pump 12 controls the level of the working fluid 16 in the fluid dispensing tip 14. The portion of the tip 14 that is not filled with working fluid 16 is filled with air or an inert gas such as nitrogen. When the system 10 retrieves sample fluid 32 from a supply and aspirates it into the tip, this air becomes an air gap 30 between the working fluid 16 and the sample fluid 32 as shown in FIG. 2. The function of the air gap 30 is to clearly show the interface 34 between the working fluid 16 and the air gap 30 and/or the interface 36 between the sample fluid 32 and the air gap 30. The air gap may be any volume but preferably ranges from 100 picoliters to 10 nanoliters. With some sample fluids, it may be desirable to use inert atmospheres such as nitrogen;

therefore, within the practice of this invention it should be understood that the air gap 30 can include air, nitrogen, or any other gas.

The amount of sample fluid aspirated is controlled by the pump 12. Preferably, the pump 12 aspirates an initial quantity of sample fluid 32 from which the final amount dispensed will be taken. The fluid dispensing tip 14 is placed close to the surface of the metering station 18. Preferably, the end 20 of the tip 14 is within a few microns of the metering station 18. A portion of the sample fluid 32 is dispensed as a sessile drop 38 onto the metering station 18. Preferably, as the sessile drop 38 is formed, it comes into contact with both the metering station 18 and the fluid dispensing tip 14. The sessile drop 38 may have a volume ranging from 10 picoliters to 10 nanoliters. Preferably the sessile drop 38 has a volume of at least twice the ultimately desired dispense volume. Larger volumes lower pressure because of their larger radii of curvature. Preferably the sessile drop 38 is larger than the inner diameter of the end 20 of the tip 14 so that the internal pressure is lowered. Preferably, the sessile drop 38 has a radius of curvature of equal to or greater than 100 $\mu$m. The pump 12 causes a portion of the sample fluid 32 in the sessile drop 38 to be re-aspirated into the tip 14. The volume of the sample fluid 32 in the tip 14 can be adjusted until it is the desired amount to be dispensed. Because of the practical nature of moving liquid surfaces very small distances within the pipette, it is often necessary to repetitively move back and forth and iterate to the desired volume in the tip. Preferably, the system can be used to dispense volumes of sample fluid 32 on the order of 1–100 picoliters, e.g., 10–25 picoliters, 25–75 picoliters, 50–100 picoliters, etc. The volume of sample fluid dispensed may be as small as 1 picoliter and as large as 10 nanoliters.

It should be understood that after the volume of sample fluid 32 is dispensed at a location or into a vessel selected by the operator, the pipette tip 14 can be reinserted into the sessile drop 38, and additional small volumes of fluid can be retrieved and dispensed in the same manner. In this instance, the pump 18 would need to initially aspirate the sample fluid 32 from the drop 38 after the pipette tip 14 is reinserted, and then the precise volume would be obtained, usually in an iterative process, as discussed above. It should also be understood that the process of this invention, which requires first forming a sessile drop of the sample fluid, then obtaining a precise volumetric sample from the sessile drop using imaging technologies, and the radius of curvature advantages of the sessile drop discussed in detail above, can be automated where by dispensing of the sessile drop, and aspiration and volumetric adjustment with imaging assistance, are both performed using computer control operations. This will allow a large number of extremely small sample volumes to be produced and processed in an automated fashion.

Figure 3:
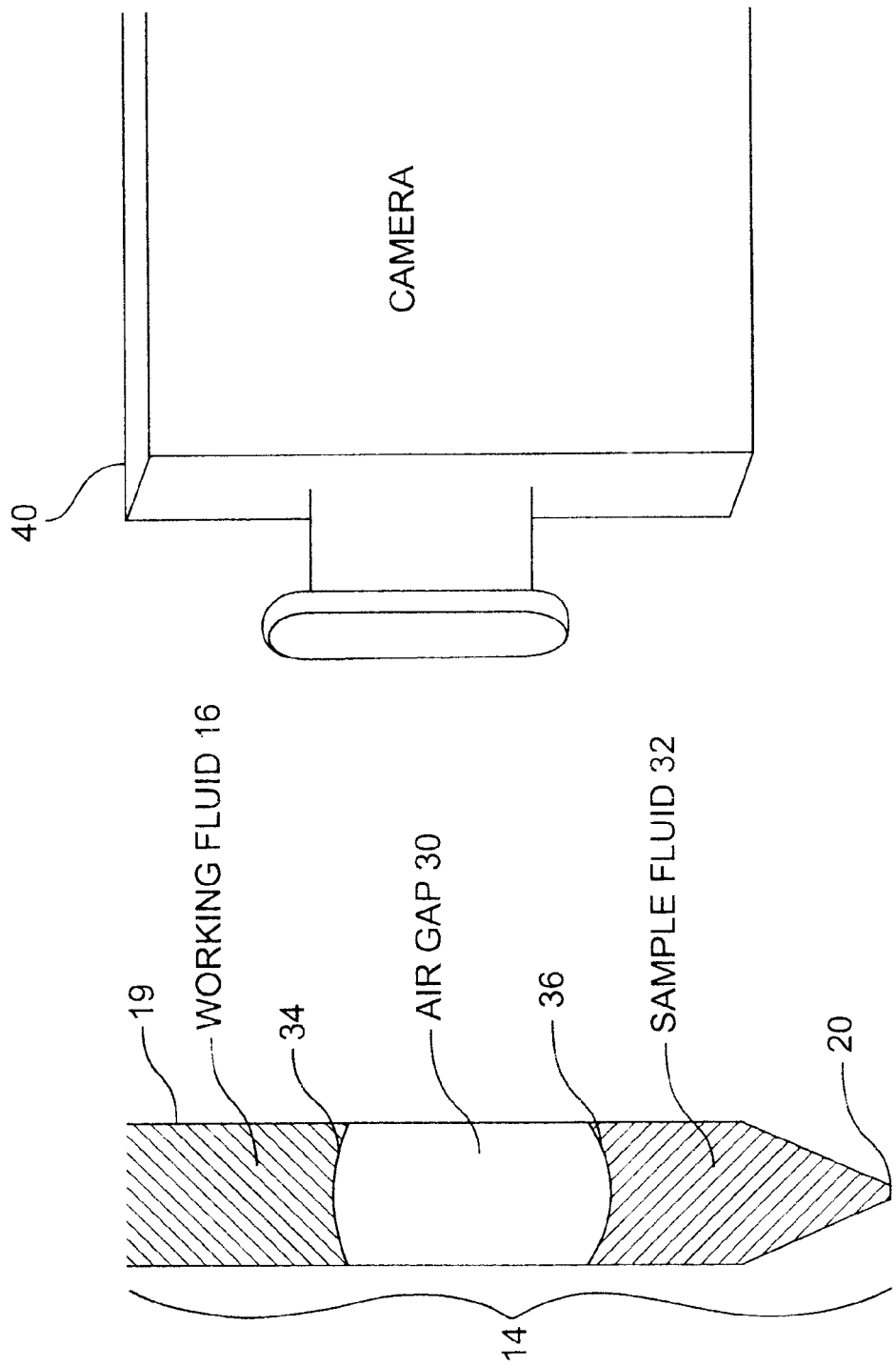
FIG. 3 is a schematic view of the tip and a camera embodying an imaging device.

The volume of the sample fluid is verified by visual inspection. As illustrated in FIG. 3, an imaging device 40 may be used to visually observe the interface 34 between the air gap and the working fluid 16 or alternatively the interface 36 between the air gap 30 and the sample fluid 32. The function of the imaging device 40, and associated computer software (not shown), is to assess the quantity of the sample fluid 32 being drawn into the tip 14 and ultimately being dispensed from the tip 14. Many conventional imaging devices and software analysis tools are available, e.g., charge coupled display (CCD) cameras, etc. A preferred embodiment for imaging device 40 is discussed in more detail below.

Figure 4:
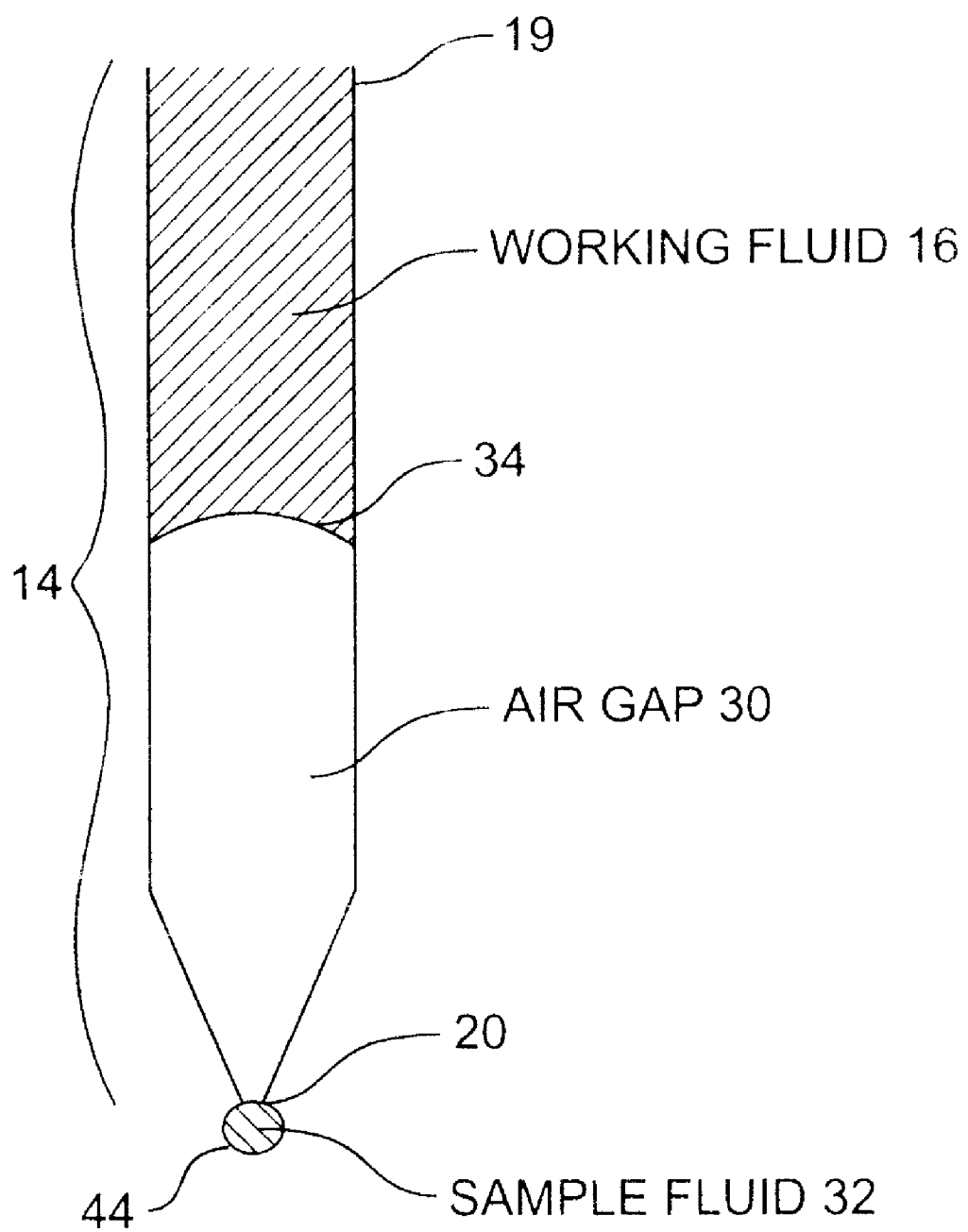
FIG. 4 is a schematic view of the tip with a hanging drop of sample fluid.

Once the correct volume of sample fluid 32 is contained in or at the tip 14, the tip 14 is withdrawn from the sessile drop 38. The tip 14 is then moved to a location where the sample fluid 32 is to be dispensed (as is best shown in FIG. 4). The sample fluid 32 is then expelled at this location. For very small volumes of fluid, there are evaporation problems if the fluid is hanging from the tip end. For example, picoliters of water can evaporate in seconds. Thus, for these very small volumes (on the order of 10 picoliters) this invention takes advantage of knowing the geometry of the tip inside ahead of time (a priori). This allows relating the height of the sample in the tip ultimately to the dispensed volume. By adjusting the liquid at the metering station, a correct volume is obtained (this may take 10 or more up and down cycles). Then all of the sample left in the tip is dispensed. This can be achieved by pumping action. Vibratory stimulation can also be used in conjunction with pumping for the same stick/slip reasons discussed above for aspiration. This allows a precise volume to be dispensed since sample fluid does not evaporate while inside the tip.

For larger volumes, e.g., nanoliter quantities, a hanging drop methodology can be used where the imaging device 40 (or a second imaging device not shown) can be used to analyze the size of the drop formed on the tip end 20. This can be done by assessing the height and diameter of the drop. The hanging drop 44 is then touched on the surface of the dispensing location, at which point the hanging drop 44 detaches from the end 20 onto the desired location.

Figure 5:
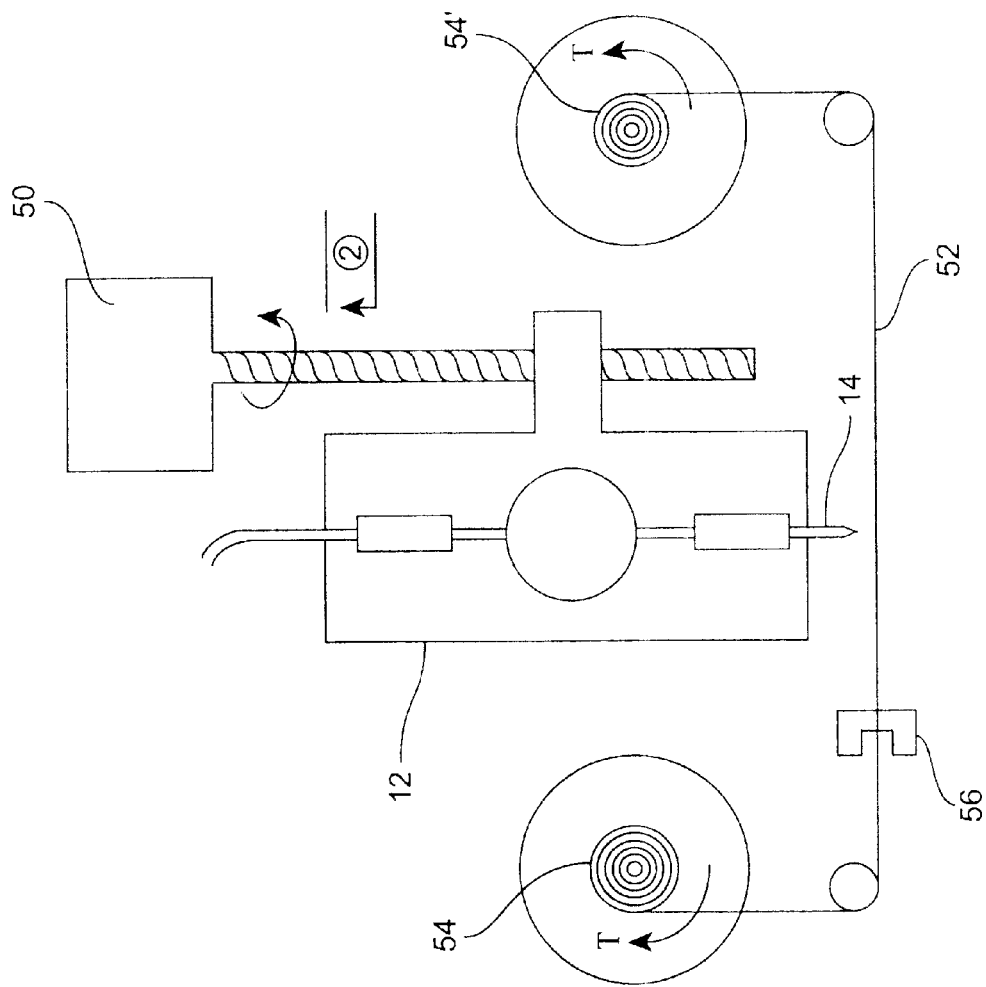
FIG. 5 is a schematic view of an embodiment of the invention where a perforated tape is used to provide a metering station for the sessile drop on an automated basis.

FIG. 5 shows a preferred embodiment of the invention which automatically provides a metering station below the pipette tip. The time to access the sessile drop for the "ruler" function is a limitation on the rapidity with which drops can be dispensed (throughput). Rather than take the dispense tip to a table using a robot, or moving a solid table under the tip, a perforated tape or other continuously supplied surface on which sessile drop formation can occur may serve as a table. One motivation is to facilitate always having a virginal surface for the new sessile drop, ensuring no cross contamination if different liquids are used.

FIG. 5 shows an embodiment where the dispensing tip 14 and pump 12 are translatable on the Z axis using a motor and lead screw combination 50 which can move the pipette tip 14 up and down, that is, within and out of contact with the sessile drop 38. Other mechanisms for Z axis movement of the pipette tip 14 may also be used in the practice of this invention. In the preferred embodiment, a tape 52, having for example dimensions of 10 mm width, indefinite length, and a repeating pattern of approximately 3 mm diameter perforation holes on, for example, 10 mm centers down the length of the tape 50 is used to provide metering stations for the sessile drops. In general, the sessile drop surface should be nonreactive and as low a surface energy as possible so the drop sits with a high contact angle. A polytetrraflouroethlyene (PTFE) or similar surface is preferred. Thus the tape 50 can be made from PTFE. In addition, it may be desirable to laminate a different polymer film on the back side of the PTFE or similar material to serve as a carrier for better mechanical stability.

The tape 50 is stretched taut by motors on the takeup and supply reels 54 and 54' (as is shown by arrows T). The takeup and supply reels 54 and 54' may move the tape 52 in one direction guiding the tape 52 from the supply reel 54' to the take up reel 54, or provision for reverse movement of the tape 50 can also be provided such that a sessile drop can be returned to a position below the pipette tip 14 at some point after its previous use. In this way, a single sessile drop can be subdivided into a large number of microscopically small drops.

An optical sensor 56 can be used to position the tape 50 below the dispensing tip 14. As discussed above, the tape 50 is perforated. This allows for significant automation of small volume sample retrieval and dispensing. First, the tape 50 is advanced to provide a virginal surface for the sessile drop. Then, a precise, small quantity volume of fluid is aspirated from the sample as described in detail above. Then, the dispense tip 14 is raised clear of the sessile drop. Then, the tape 50 is advanced again after the small volume of fluid is obtained from the sessile drop until the dispense tip 14 is positioned over a perforation (this can be determined using the optical sensor 56 and controller (not shown). Finally, the tip 14 is lowered through the hole in the tape 50 down to the user's surface for dispensing and is dispensed thereon as described above (see FIG. 4).

The advantages of this scheme are as follows:

1) The tip only needs one axis, "Z", so its mechanism stays simple and light. This facilitates rapid motion. Preferably, a separate user-supplied robot carries the whole apparatus to the desired location under the dispense mechanism, or brings desired surfaces under the dispense unit.
2) The tape can be rapidly advanced, hole to surface, or surface to hole.
3) The tape facilitates an indefinite (meaning large) number of new surfaces for sessile drops to prevent cross contamination.
4) When desired, a single sessile drop can be returned under the tip for further dispense volume ruling, so a single sessile drop can be subdivided into an indefinite number of microscopically small drops.
5) When finished, the remaining sessile drop liquid can simply be rolled up into the takeup reel side spool 54 for disposal. The liquid amounts are small enough that they do not leak out of the spool.

Figure 6:
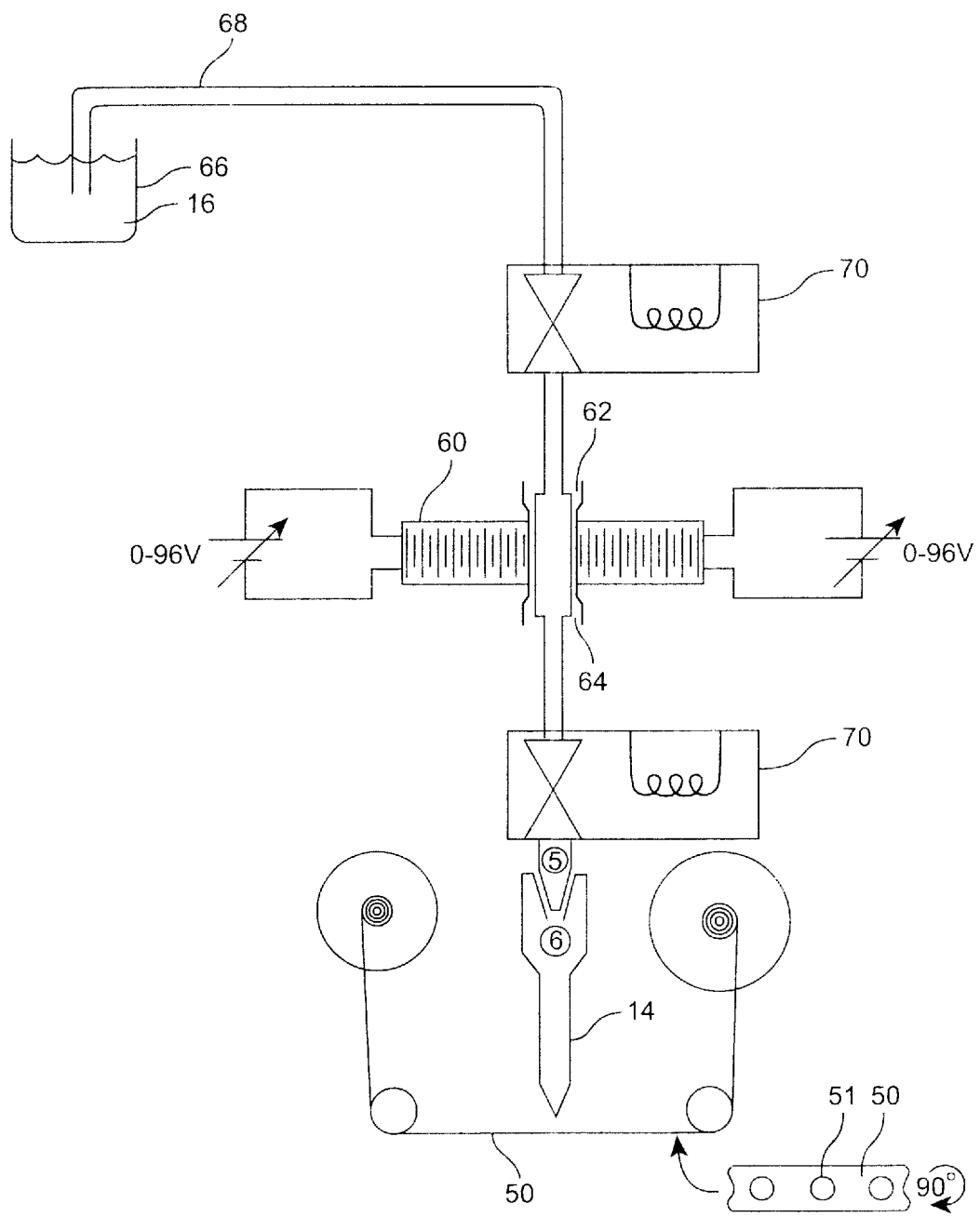
FIG. 6 is a schematic view of showing a piezo pumping configuration in combination with the perforated tape feature of FIG. 5.

FIG. 6 shows an embodiment of the invention where a dual diaphragm piezoelectric pump 60 is used for the aspiration and precise volumetric adjustments to the sample fluid volume to be dispensed, as discussed in conjunction with FIG. 1 (which shows a pump generally as 12). In operation, it is preferable to use a high capacity piezo pump where both ends of the internal cylinder are piezo driven diaphragms. High capacity is means that the pump can displace enough volume (e.g., 10 microliters) that it can self-prime. The pumping system preferably includes of a high-capacity piezo pump with a micro valve on its inlet 62 and outlet 64. By opening and closing the valves appropriately, the pump 60 can flow liquid indefinitely in either direction. In this mode it acts similar to an internal combustion engine, with an "intake" and an "exhaust" cycle. It should be understood that the liquid handling pumping system used in the practice of this invention may comprise a piezo pump backed by a syringe pump, or it may be comprised of simply of a high-capacity piezo pump 60 as shown in FIG. 6.

The reason capacity must be considered is that the valves, even though they are "micro", displace a certain volume as they open or close. If this valve "internal volume" is similar or greater than the pump's, it is very difficult to pump liquid indefinitely in either direction. Instead it sloshes back and forth between the valve and the pump. When the pump exceeds the valve by several times, pumping is acceptably efficient and it "works" from the user's point of view. Finally, "pump indefinitely in either direction," should be understood to mean the pump is capable of moving all of the liquid from one glass to another, in the ordinary sense. For example, it may do this 10 microliters per cycle and a cycle takes 100 milliseconds, but it can be done in many cycles. When the valve capacity is excessive compared to the pump, the fraction of liquid, compared to the pump's internal volume (e.g., 10 microliters), that actually moves through drops rapidly from close to 100% to close to 0%.

In FIG. 6, the user supplied system fluid or "working fluid" 16 is retrieved from vessel 66 using tubing 68. The tubing 68 may be microbore polyvinyl chloride tubing, such as 0.042" internal diameter tubing available from Lee as TUVA42220900A. However, it should be understood that variations in tubing selection and that other transport mechanisms can be substituted for the tubing. Solenoid microvalves 70 are positioned on the inlet 62 and outlet 64 sides of the piezo pump 60. These microvalves 70 may be, for example of the type Lee INKA 1224212H or any other suitable type. As noted above, the piezo pump 60 is used for aspirating and dispensing operations, and works in conjunction with the microvalves 70 to allow pumping indefinitely in either direction.

The dispensing tip 14 may be a disposable tip that is connected below the microvalve 70 on the outlet 64 side of the piezo pump 60. If a disposable tip configuration is desired, a hub or fitting 72, such as Leur fitting, can be used for easy attachment and detachment of the dispensing tip 14. As discussed in conjunction with FIG. 5, the tape 50, which may be perforated polyethylene/PTFE tape, is moved under the dispensing tip 14 in an automated fashion. Thus, the piezo pump 60, movement of the tape 50, and sessile drop formation, sample retrieval, and subsequent dispensing operations through perforations 51 in the tape 50 can proceed in an automated fashion.

Various materials can be used for the dispensing tip 14, including drawn glass capillaries (hollow glass tubing that is pulled out while hot, much like a glass blower in Venice would have done it 500 years ago) and also fused silica tubing. The fused silica tubing is very strong but not really transparent. However, it is translucent and an acceptable image can be obtained by using a strong LED light source behind the silica tube. Therefore, it should be understood that it is not necessary that the dispense tip 14 be limited to glass. It merely needs sufficient light transmission that a shadow of the liquid inside the tip can be detected while at the sessile drop "ruler" station.

As noted above, tapered tips give an extremely wide volume holding range for a modest change in Z level of the top of the liquid. This is because volume is proportional to cross-sectional area and the area increases proportionally to the radius squared. A tapered tip 14 gives much higher incremental volume as the tip diameter grows. The reason we "see" the liquid inside the dispense tip 14 is that this is a refraction image, i.e., a silhouette. The liquid will have (reliably) a different index of refraction than the glass or silica tube wall. In the case of a round tube being used as the tip 14, the shape is curved and the curved light interface refracts and pushes the backlight away from the detector. The liquid appears dark because there is no light coming from that region as it was directed, or bent, away.

The exact tip 14 location, to accuracies of a few microns, can be determined by image analysis while the tip is within the sessile drop "ruler" view (FIG. 2 shows the tip 14 in the sessile drop 38). This is handy because each new tip 14 will fall at a slightly different location when the user replaces tips. Different users may wish to place these nano and picoliter drops with micron precision on targets that might be only 10's of microns across, which is far too small to see with the naked eye. The image analysis measurement is useful because, in the preferred embodiment and as discussed in conjunction with FIG. 5, the tip has only one axis of motion, Z, up and down, and so reporting the exact location to the user robot allows fine tuning of the eventual deposition. The Z axis "holds" the X–Y position as it goes up and down. A two-dimensional image of the tip and sessile drop might give us, say, the "Z" (up and down) and "X" (left and right) axis positions of the tip, but does not provide the "Y", or in and out location along the viewing axis. This can preferably be obtained with an "Autofocus" such as that shown in FIG. 7.

Figure 7:
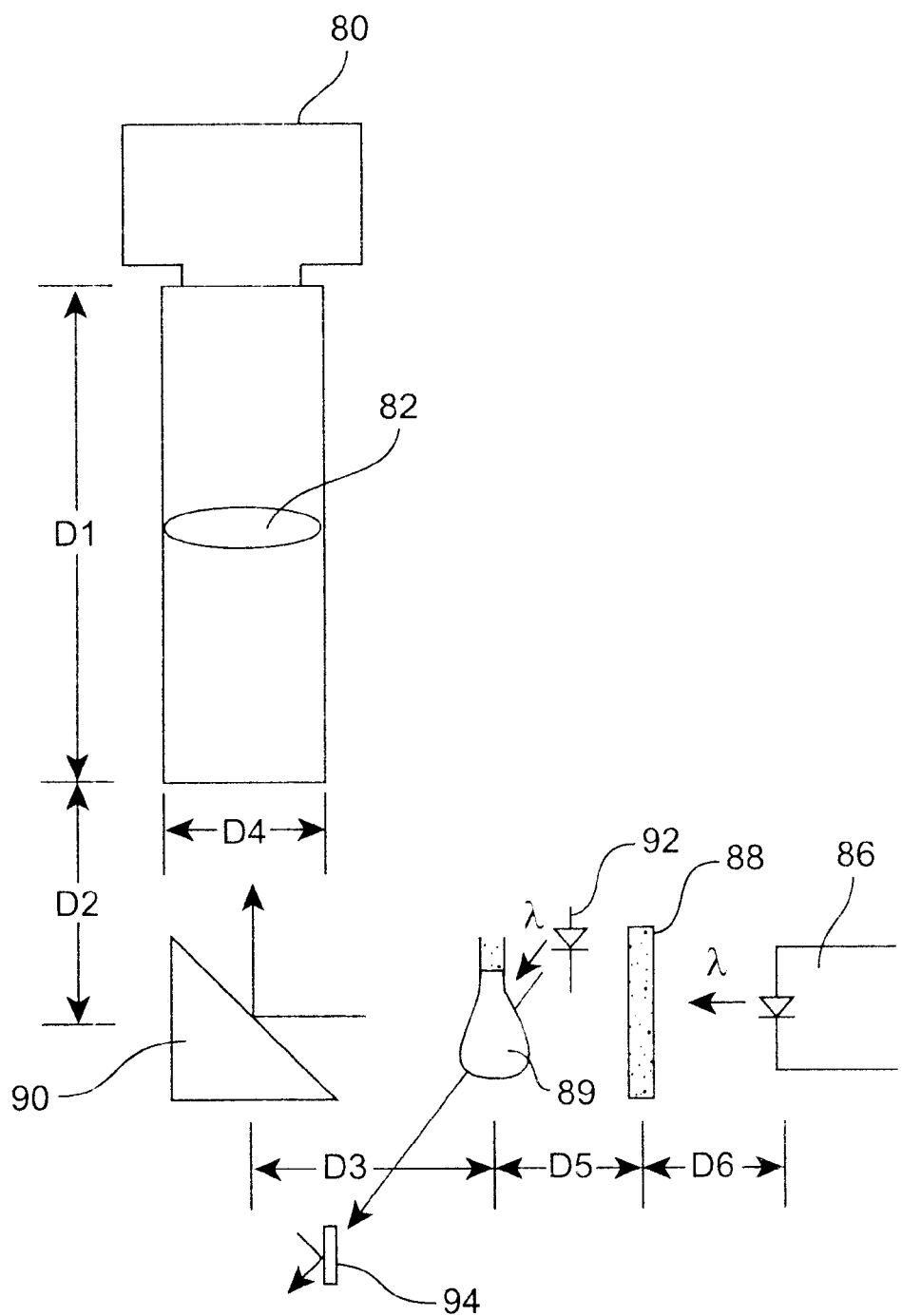
FIG. 7 is a schematic view of a focusing feature of the invention used to determine the droplet size which is to be dispensed.

FIG. 7 shows a camera 80 positioned above a microscope lens 82 that is 90° out of alignment with the drop 84 being imaged. Light from LED 86 passes through a diffuser 88, the drop 84, and prism 90, and is then directed up to the camera. A number of conventional pieces of equipment may be used in the configuration shown in FIG. 7. For example, the LED 86 may be a Lumex SSL-LX50939RC/E, 5 mmφ×15 mm;the diffuser 88 may be a typical ground glass devices such as that which is available from Edmund Scientific as L32-333, 15 mm×21 mm; the prism 90 is a 90° turning mirror prism, such as a type Edmund Scientific L32-333, 15 mm×21 mm; the microscope lens may be a Navistar 1-61449+1-61445; and the camera 80 may be a USB camera. D1 designates the mechanical length of the lens, and may be, for example, type 115 mm. D2 and D3 constitute the working distance of the lens, and may be, for example, 93 mm and 51 mm or 93 mm and 113 mm. D3 must be enough for the lens body to clear the pump. D4 may be, for example 29 mm, as is the case in the Navitar "precision eye" lens. D5 is the distance focal plane to light diffuser and should be a distance sufficient to collimate late, such as, for example 10 mm. D6 is the distance from the LED 86 to the diffuser 88, and may be 5 mm. Of course, the dimensions can be varied within the practice of this invention. The presence of a drop 84 can be detected using an emitter 92-detector 94 pair.

By having a stepper motor on the microscope focus element, best focus position (which will happen to be when the center of the tip is in the focal plane) can be related to a stepper motor step count. The step count will preferably have been previously calibrated with the physical location of the focal plane. In this way, "Y" can be extracted. This extraction of "Y" information is good enough to be useful in positioning the tip 14. Of course, other means for locating the position of the tip 14 are possible within the practice of this invention.

In the preferred embodiment shown in FIG. 7, the same camera, i.e., imaging device, that measures liquid volume in the tip also can measure the mechanical location of the tip. Z and X are obvious in the image, but Y is not, if I assume Y is measured along the viewing axis of the camera (i.e., perpendicular to the focal plane that contain Z and X). So the same imaging device can measure volumes and also fix the tip positioning with respect to the reference frame of the apparatus. Its accuracy (resolution) is better in Z and X, but it is still acceptable in Y as long as you can calibrate the motor position to the physical lens position. Focusing is accomplished by moving the first lens inside the microscope back and forth, along the Y axis. A motor can drive this mechanism. The actual distance from the first glass surface to the focal plane is the working distance of the microscope. This is known, a datasheet value. If I know the mechanical position of the first glass surface, from the motor drive, then I know where the focal plane lies—which is the Y location of the tip central axis if I have focused on the tip apex (which is recommended).

There are several points in the drop image that fall within the plane through the central axis of the tip. We choose those points for our autofocus. The autofocuss can be understood better with reference to a little geometry. Image the tip as a cylindrically symmetric device about a vertical central axis. We locate the tip by the X and Y positions of this central axis. This central axis is right down the bore of the tube. The bottom of the tip sets the Z location. As the tip moves up and down, its X and Y positions do not change (assuming a well constructed device). We say X is sideways in the image and Y is the perpendicular axis we can not directly see in the image—its position is what sets focus. If the tip's Y value happens to fall in the focal plane (an X–Z plane the "working distance" from the first glass surface), then the image is in focus. The utility of all this is that I can report to the host, or user, robotic controller the exact X, Y, and Z values of the tip apex. That controller can measure from my mounting surface and figure out (by simple algebra) where to move me or the same so the tip can be precisely positioned over the desired location on the sample.

Other imaging and movement mechanisms may also be employed within the context of this invention.

While the invention has been described in terms of its preferred embodiments. Those skilled in the art will recognize that the invention can be practiced with modification within the spirit and scope of the appended claims.

I claim:

1. An apparatus for dispensing specified volumes of fluid, the apparatus comprising:

a fluid dispensing tip;

a pump for aspirating fluid within said fluid dispensing tip, and for forcing said fluid to be dispensed from said fluid dispensing tip;

a tape having an inert surface positioned to receive sample fluid in the form of a drop of a first volume from said fluid-dispensing tip, said tape being translatable under said fluid-dispensing tip so as to receive multiple drops of sample fluid at multiple locations; and means for selectively retrieving a second volume of said sample fluid from said drop on said metering station which is smaller than said first volume and dispensing said second volume of said sample fluid at a desired location.

2. The apparatus of claim 1 wherein said tape has apertures therethough, and wherein said means for selectively retrieving and dispensing said second volume causes said fluid dispensing tip to pass through at least one of said apertures during dispensing of said second volume.

3. The apparatus of claim 1 wherein said dispensing tip is translatable in a Z-axis.

4. The apparatus of claim 1 wherein said fluid dispensing tip is configured to contain 1 picoliter to 10 nanoliters of a sample fluid at an end, an air gap positioned above the sample fluid, and a working fluid positioned above said air gap.

5. The apparatus of claim 4 wherein said pump is adapted to maintain said working fluid in said fluid-dispensing tip and adapted to aspirate said first volume of said sample fluid into said fluid dispensing tip and expel said first volume of said sample fluid from said fluid dispensing tip.

6. The apparatus of claim 5 wherein said pump is a piezo pump.

7. The apparatus of claim 1 wherein said pump is a piezo pump.

8. The apparatus of claim 1 wherein said dispensing tip is transparent or translucent, and said means for selectively retrieving and dispensing said second volume of sample fluid includes an imaging device which is used to detect an interface in said dispensing tip of an air gap and a fluid.

9. The apparatus of claim 8 further comprising a means for autofocussing on a drop of sample fluid being expelled from said dispensing tip.

10. The apparatus of claim 1 further comprising a means for advancing said tape in at least one direction.

11. The apparatus of claim 1 further comprising a means for advancing said tape in at least two opposite directions.

* * * * *